United States Patent [19]

Quarroz

[11] Patent Number: 4,496,733

[45] Date of Patent: Jan. 29, 1985

[54] PROCEDURE FOR PRODUCING 2-AMINOPYRIDINES FROM 2-PYRIDINE CARBOXYLIC ACID-N-OXIDES

[75] Inventor: Daniel Quarroz, Visp, Switzerland

[73] Assignee: Lonza Ltd., Basel, Switzerland

[21] Appl. No.: 480,314

[22] Filed: Mar. 30, 1983

[30] Foreign Application Priority Data

Mar. 31, 1982 [CH] Switzerland .......................... 1979/82

[51] Int. Cl.³ .......................................... C07D 213/73
[52] U.S. Cl. ..................... 546/310; 546/311
[58] Field of Search ................. 546/311, 310

[56] References Cited

PUBLICATIONS

*Ullmann Encyclopedia of Technical Chemistry*, 4th Edition, vol. 19, p. 602.
*Beilstein*, vol. 22, p. 542.

*Primary Examiner*—Jane T. Fan
*Attorney, Agent, or Firm*—Fisher, Christen & Sabol

[57] ABSTRACT

Procedure for producing 2-aminopyridines having general formula:

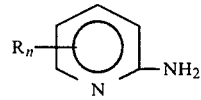

from 2-pyridine carboxylic acid-N-oxides having the formula:

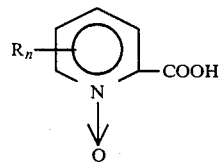

wherein R is H or a —COOH group or an alkyl group having $C_1$ to $C_8$ or an aryl group, and n is a number between 1 and 4. The 2-pyridine carboxylic acid-N-oxide is converted with a lower aliphatic carboxylic acid anhydride and a tertiary amine in the presence of a carboxylic acid nitrile. The conversion product is hydrolyzed to the 2-aminopyridine compound.

10 Claims, No Drawings

PROCEDURE FOR PRODUCING 2-AMINOPYRIDINES FROM 2-PYRIDINE CARBOXYLIC ACID-N-OXIDES

BACKGROUND OF THIS INVENTION

1. Field of this Invention

The invention relates to a process for producing 2-aminopyridines, and particularly 2-aminopyridine carboxylic acids. This invention also relates to a composition for conducting such process.

2. Prior Art

Producing 2-aminopyridines by converting pyridines with sodium amide at increased temperature is known. Such synthesis is known as the "Tschitschibabin reaction" (see *Ullmann Encyclopedia of Technical Chemistry*, 4th Edition, Vol. 19, p. 602). Dealing with sodium amide is unpleasant since it is a substance which irritates the skin and the mucous membranes. Furthermore, the conversion of 2-chloronicotinic acid to 2-aminonicotinic acid by means of $NH_3$ at 170° C. is known (*Beilstein*, Vol. 22, p. 542). The yield is approximately 50 percent.

BROAD DESCRIPTION OF THIS INVENTION

An object of this invention is to produce 2-aminopyridine carboxylic acid and 2-aminopyridines using an effective and simple procedure. Another object of this invention is to provide compositions from which to produce such products. Other objects and advantages of this invention are set out herein or are obvious herefrom to one ordinarily skilled in the art.

The objects and advantages of this invention are achieved by the processes and compositions of this invention.

This invention broadly involves converting 2-pyridine carboxylic acid-N-oxide with a lower aliphatic carboxylic acid anhydride and a tertiary amine in the presence of a carboxylic acid nitrile and then saponifying the 2-acylamidopyridine which has been formed.

This invention further involves a procedure for producing a 2-aminopyridine having the formula:

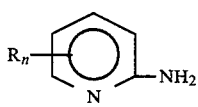

from a 2-pyridine carboxylic acid-N-oxide having the formula:

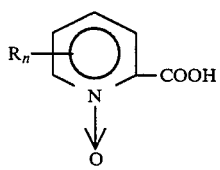

wherein R is H or a —COOH group or an alkyl group having $C_1$ to $C_8$ or an aryl group and n is a number between 1 and 4. The process includes converting such 2-pyridine carboxylic acid-N-oxide with a lower aliphatic carboxylic acid anhydride and a tertiary amine in the presence of a carboxylic acid nitrile and hydrolysing the conversion product into such 2-aminopyridine.

Acetic acid anhydride, propionic acid anhydride and pivalic acid anhydride (i.e. Trimethylacetic acid anhydride), in particular, and preferably acetic acid anhydride, are used as the lower aliphatic carboxylic acid. In general, the lower aliphatic carboxylic acid anhydrides have the formula $(RCO)O(OCR^1)$, wherein R and $R^1$ are the same or different straight or branched alkyl groups having 1 to 8 carbon atoms. Relative to the pyridine carboxylic acid-N-oxide, the carboxylic acid anhydride is used in a 1 to 10-fold molar excess, and it can serve as a solvent.

The carboxylic acid nitrile ($RC\equiv N$) can be an aliphatic nitrile, advantageously having 1 to 8 carbon atoms, which can be saturated or unsaturated; and aromatic nitrile can be used as the carboxylic acid nitrile. The carboxylic acid nitrile can be acrylonitrile, caprylonitrile, glutaronitrile, methylglutaronitrile or benzonitrile, however, it preferably is methyl cyanide. Advantageously 15 to 80 moles of the carboxylic acid nitrile are used per mole of the N-oxide.

The tertiary amine can be an aliphatic or aliphatic-/aromatic tertiary amines, such as, tributylamine, 2,6-lutidine or pyridine, however, triethylamine is preferred. The ratio of tertiary amine to pyridine carboxylic acid-N-oxide is between 1 to 1 and 20 to 1, and preferably from 5 to 1 to 2 to 1. The tertiary amine has the formula $RR^1R^2N$ wherein R, $R^1$ and $R^2$ are the same or different branched or straight alkyl groups usually having 1 to 8 carbon atoms or aryl groups (e.g., $C_6H_5$—).

Surprisingly, 2-aminopyridine compounds in high yields are obtained using the procedure of this invention with the reaction readily taking place at great speed and relatively low temperatures.

In addition to 2-pyridine carboxylic acid-N-oxide, other corresponding pyridine carboxylic acid-N-oxides, such as, pyridine dicarboxylic acid-(2,3)-N-oxide, (i.e., quinolinic acid), pyridine dicarboxylic acid-(2,4)-N-oxide, (i.e., lutidinic acid), pyridine dicarboxylic acid-(2,5)-N-oxide, (i.e., isocinchomeronic acid) and pyridine carboxylic acid-(2,6)-N-oxide, (i.e., dipicolinic acid), and the corresponding pyridine tricarboxylic acid-N-oxides, such as, pyridine tricarboxylic acid-(2,3,4)-N-oxide, (i.e., α-carbocinchomeronic acid), pyridine tricarboxylic acid-(2,4,5)-N-oxide, (i.e., berberonic acid), pyridine tricarboxylic acid-(2,4,6)-N-oxide (i.e., trimesitic acid) and pyridinepentacarboxylic acid-N-oxide, can be used as the starting material. Furthermore, the pyridine carboxylic acid-N-oxides above cited can be nucleus-substituted 1 to 4-fold with alkyls having a chain length of one to eight carbon atoms or with aryls. The aryl group is typically $C_6H_5$— or naphthyl.

The conversion reaction is carried out at a temperature of from −20° to 90° C. and preferably from 20° to 80° C.

This invention further involves a composition containing (i) 2-pyridine carboxylic acid-N-oxide having the formula:

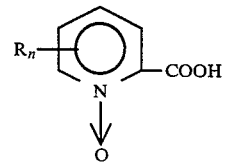

(ii) a lower aliphatic carboxylic anhydride, (iii) a tertiary amine, and (iv) a carboxylic acid nitrile.

By way of summary, this invention involves producing a 2-aminopyridine from a 2-pyridine carboxylic acid-N-oxide by converting the latter with acetic acid anhydride (or other carboxylic acid anhydride), a tertiary amine and a carboxylic acid nitrile.

DETAILED DESCRIPTION OF THIS INVENTION

As used herein, all percentages, ratios and proportions are on a weight basis unless otherwise stated herein or otherwise obvious herefrom to one ordinarily skilled in the art.

EXAMPLE 1

Production of 2-amino-5-pyridine carboxylic acid from isocinchomeronic acid-N-oxide (ICSO).

13 g of acetic acid anhydride (0.15 mole), 30 g of triethylamine (0.3 mole) and 100 g of $CH_3CN$ (2.43 mole) were put into a flask, and 18.3 g of ICSO (0.1 mole) was added in portions, at 40° C., so that $CO_2$ actively evolved. After the addition had been completed, the reaction was allowed to continue at 40° C. for approximately another hour until no more $CO_2$ was escaping. The resultant brownish-black solution was evaporated in a Rotavapor (30 Torr, 60° C.) and the viscous residue was saponified for 2 hours by adding 10 percent KOH (final pH, approximatley 12) at 80° C. To remove the triethylamine, the liquid reaction mixture was distilled and the residue acidified with concentrated HCl (pH, 5.6). The deposit produced in this way was then filtered off by means of a funnel, washed with $H_2O$ and dried at 45° C., 20 torr. The yield was 6.8 g (titrimetrically determined content, 99.5 percent) of 2-amino-5-pyridine carboxylic acid, which corresponds to 49 percent of that expected according to theory. The mother liquor was acidified to pH 1.5. An additional 1.1 g of 6-hydroxynicotinic acid (content, 95 percent) was precipitated—the yield was 8 percent relative to the ICSO.

EXAMPLES 2 TO 19

The Table sets out the conditions, reactants and results of Examples 2 to 19, which were conducted using the procedure of Example 1. In the Table, (1) means that the final product was obtained by extraction from the basic environment. Considerable quantities of the corresponding hydroxy product were often obtained as a by-product in the synthesis of the aminopyridine compounds. Thus, in Example 15, 40 percent of 2-hydroxypyridine and in Example 17, 22 percent yield of 2-hydroxypyridine carboxylic acid-3, etc., are obtained.

The total yield of amino and hydroxypyridine compounds is in the general area of from 60 to 75 percent.

TABLE

| Example No. | Educt, 1 mole | Anhydride, moles | Amine, moles | Nitrile, moles | Temp., °C. | Yield, % |
|---|---|---|---|---|---|---|
| 2 | ICSO | 1.5 acetic acid anhydride | 3 Et₃N | 20 CH₃CN | 0°–5° | 45.5 ANS |
| 3 | ICSO | 1.5 acetic acid anhydride | 3 Et₃N | 73 CH₃CN | 40° | 56.5 ANS |
| 4 | ICSO | 5.0 acetic acid anhydride | 3 Et₃N | 24 CH₃CN | 40° | 45.0 ANS |
| 5 | ICSO | 1.5 acetic acid anhydride | 7 Et₃N | 24 CH₃CN | 40° | 56 ANS |
| 6 | ICSO | 1.5 acetic acid anhydride | 3 Et₃N | 24 CH₃CN | 60°–65° | 53 ANS |
| 7 | ICSO | 1.5 acetic acid anhydride | 3 Et₃N | 24 CH₃CN | 75°–80° | 48.5 ANS |
| 8 | ICSO | 1.5 acetic acid anhydride | 3 Et₃N | 24 CaPCN | 40° | 14 ANS |
| 9 | ICSO | 1.5 acetic acid anhydride | 3 Et₃N | 20 MCN | 40° | 32 ANS |
| 10 | ICSO | 1.5 acetic acid anhydride | 3 Et₃N | 38 CH₂=CHCN | 40° | 44 ANS |
| 11 | ICSO | 1.5 acetic acid anhydride | 3 Et₃N | 23 Benzonitrile | 40° | 24.5 ANS |
| 12 | ICSO | 1.5 acetic acid anhydride | 3 Bu₃N | 24 CH₃CN | 40° | 45 ANS |
| 13 | ICSO | 1.5 acetic acid anhydride | 3 2,6-lutidine | 24 CH₃CN | 40° | 33 ANS |
| 14 | ICSO | 2 pivalic acid anhydride | 3 Et₃N | 24 CH₃CN | 40° | 39 ANS |
| 15 | PCO | 1.5 acetic acid anhydride | 3 Et₃N | 24 CH₃CN | 40°–45° | 29 2-aminopyridine (1) |
| 16 | MPCO | 1.5 acetic acid anhydride | 3 Et₃N | 24 CH₃CN | 40°–45° | 18 2-amino-6-methyl-pyridine (1) |
| 17 | CSO | 1.5 acetic acid anhydride | 3 Et₃N | 24 CH₃CN | 40°–45° | 23 APS-3 |
| 18 | LSO | 1.5 acetic acid anhydride | 3 Et₃N | 24 CH₃CN | 40°–45° | 50 APS-4 |
| 19 | OCSO | 1.5 acetic acid anhydride | 3 Et₃N | 24 CH₃CN | 40°–45° | 34 AC (1) |

TABLE-continued

| Example No. | Educt, 1 mole | Anhydride, moles | Amine, moles | Nitrile, moles | Temp., °C. | Yield, % |
|---|---|---|---|---|---|---|
| | | hydride | | | | |

NOTES:
ICSO = Isocinchomeronic acid-N—oxide
PCO = Picolinic acid-N—oxide
MPCO = 6-methylpicolinic acid-N—oxide
CSO = Quinolinic acid-N—oxide
LSO = Lutidinic acid-N—oxide
DPSO = Dipicolinic acid-N—oxide
CCSO = 2-quinoline carboxylic acid-N—oxide or quinaldine acid-N—oxide
Et₃N = Triethylamine
Bu₃N = Tributylamine
CaPCN = Caprylonitrile
MGN = Methylglutaronitrile
ANS = 2-Aminopyridine-5-carboxylic acid
APS-3 = 2-Aminopyridine-3-carboxylic acid
APS-4 = 2-Aminopyridine-4-carboxylic acid
AC = 2-Aminoquinoline

What is claimed is:

1. Process for the production of a 2-aminopyridine having the formula:

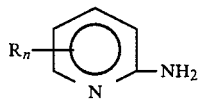

from a 2-pyridine carboxylic acid-N-oxide having the formula:

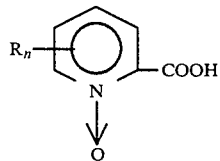

wherein R is H or a —COOH group or an alkyl group having one to eight carbons or an aryl group, and n is a number between 1 and 4, comprised of converting said 2-pyridine carboxylic acid-N-oxide with a lower aliphatic carboxylic acid anhydride and a tertiary amine in the presence of a carboxylic acid nitrile, an intermediate conversion product resulting, and hydrolysing said intermediate conversion product, said 2-aminopyridine resulting.

2. Process as claimed in claim 1 wherein the lower aliphatic carboxylic acid anhydride is acetic acid anhydride.

3. Process as claimed in claim 1 wherein the tertiary amine is triethylamine.

4. Process as claimed in claim 1 wherein the aliphatic carboxylic acid nitrile has from 1 to 8 carbon atoms in the aliphatic group or is an aromatic carboxylic acid nitrile.

5. Process as claimed in claim 1 wherein there are 1 to 5 moles of the lower carboxylic acid anhydride, 3 to 7 moles of the tertiary amine and 15 to 80 moles of carboxylic acid nitrile per mole of the 2-pyridine carboxylic acid-N-oxide.

6. Process as claimed in claim 1 wherein the conversion is conducted at a temperature of from −20° to 90° C.

7. Process as claimed in claim 1 wherein the conversion is conducted at a temperature of from 20° to 80° C.

8. Process for the production of a 2-aminopyridine having the formula:

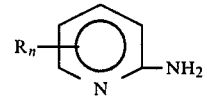

from a 2-pyridine carboxylic acid-N-oxide having the formula:

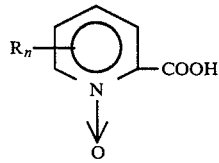

wherein R is H or a —COOH group or an alkyl group having one to eight carbons, and n is a number between 1 and 4, comprised of converting said 2-pyridine carboxylic acid-N-oxide with a lower aliphatic carboxylic acid anhydride and a tertiary amine in the presence of a carboxylic acid nitrile, an intermediate conversion product resulting, and hydrolyzing said intermediate conversion product, said 2-aminopyridine resulting.

9. Process as claimed in claim 8 wherein R is H.

10. Process as claimed in claim 8 wherein R is a —COOH group.

* * * * *